(12) United States Patent
Kelkar et al.

(10) Patent No.: US 6,521,784 B2
(45) Date of Patent: Feb. 18, 2003

(54) PROCESS FOR THE PREPARATION OF ACETIC ACID OR METHYL ACETATE

(75) Inventors: Ashutosh Anant Kelkar, Maharashtra (IN); Sunil Sopana Tonde, Maharashtra (IN); Sunil Sadashiv Divekar, Maharashtra (IN); Raghunath Vitthal Chaudhari, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/774,246

(22) Filed: Jan. 30, 2001

(65) Prior Publication Data

US 2002/0103397 A1 Aug. 1, 2002

(51) Int. Cl.⁷ .............................................. C07C 67/00
(52) U.S. Cl. ........................................ 560/239; 562/538
(58) Field of Search ............................ 560/239; 562/538

(56) References Cited

U.S. PATENT DOCUMENTS 5,396,011 A * 3/1995 Kuhn et al.
5,679,837 A * 10/1997 Shinoda et al.

* cited by examiner

Primary Examiner—Samuel Barts
(74) Attorney, Agent, or Firm—Darby & Darby

(57) ABSTRACT

Methanol is reacted in presence of catalyst system comprising of an iron containing compound and a tin containing compound with or without an organic compound containing C, N, O, P, S, diamine, diketone, and or diphosphines as a ligand to produce acetic acid or methyl acetate. The reaction is effected in a solvent containing nitro or nitrite group.

30 Claims, No Drawings

PROCESS FOR THE PREPARATION OF ACETIC ACID OR METHYL ACETATE

FIELD OF THE INVENTION

The present invention relates to a process for the preparation of acetic acid or methyl acetate.

An iron and a tin containing compound as a catalyst is reported for producing acetic acid and or methyl acetate from methanol with high activity without an iodide promoter and without carbon monoxide in one pot reaction. The present invention relates to a process for production of acetic acid and or methyl acetate in the presence of catalyst system comprising of an iron containing compound and a tin containing compound with or without an organic compound containing C, N, O, P, S, diaminie, diketone, and or diphospliines as a ligand, with methanol as a reactant and nitrile or nitro compound as a solvent.

BACKGROUND OF THE INVENTION

Acetic acid has been produced industrially on a large scale by methanol carbonylation by the well-known Monsanto and Cativa TM processes. References may be made to U.S. Pat. No. 3,816,490A, EP 728726A1, EP 752406A1, wherein rhodium or iridium is used as catalyst to produce acetic acid using methanol and carbon monoxide. The drawbacks are the catalysts used in these processes are highly expensive. The processes also use an iodide promoter, which causes corrosion of the reactor and downstream equipments. Further, the need of high purity carbon monoxide as a reactant restricts the conditions of location of the plant. In addition the reaction is usually effected in liquid phase containing water consuming high energy to separate the product acetic acid. Nickel containing catalysts are also active for the carbonylation of methanol. Reference may be made to U.S. Pat. No. 4,902,659, wherein the nickel containing catalysts are reported for the production of acetic acid. The drawbacks are the use of iodide promoters, which causes corrosion of the reactor and downstream equipments. Further, the need of high purity carbon monoxide as a reactant restricts the conditions of location of the plant. In addition the reaction is usually effected in liquid phase containing water consuming high energy to separate the product acetic acid. The use of Ru—Sn heteronuclear cluster compounds has also been proposed. Reference may be made to J. Chem. Soc. Chem. Commun. 1511–1512(1990) wherein Ru—Sn heteronuclear cluster compounds containing an anion comprising of $[Ru(SnCl_3)_5L]^{3-}$ (wherein L represents a ligand) as a catalyst for producing acetic acid and or methyl acetate from methanol in absence of CO in one stage reaction in liquid phase has been suggested. The drawbacks are the above-mentioned heteronuclear clusters contain Ruthenium, which is expensive and the solubility of the anionic cluster is very low in methanol, methyl acetate, acetic acid and other organic solvents. Also the catalyst precipitates out during reaction due to formaldehyde formed as an intermediate product. Thus catalyst deactivation takes place within a short period of reaction time. In particular, the catalyst is liable to be deactivated at higher temperature. A ruthenium containing catalyst has been suggested for producing acetic acid and or methyl acetate from methanol, methyl formate, and or Para formaldehyde. Reference can be made to EP 0631814A1 wherein the ruthenium catalyst having general formula $Ru(SnY_3)_m(L)_n$ (wherein Y represents a halogen atom, a alkyl group, an aryl group, an aralkyl group or an alkoxyl group, L represents a ligand, m is an integer of 1 to 6, n is an integer of 0 to 5 and m+n is an integer of 1 to 6) is active for the conversion of methanol to acetic acid or methyl acetate. The drawbacks are the above mentioned heteropolynuclear complexes contain expensive ruthenium and the solubility of the anionic cluster is very low in methanol methyl acetate, acetic acid and other organic solvents.

OBJECT OF THE INVENTION

The main object or the present invention is to provide a process for acetic acid or methyl acetate which obviates the drawbacks as detailed above.

Another object of the present invention is to provide a cheaper catalyst for the production of acetic acid or methyl acetate from methanol.

Still another object of the present invention is to provide a noncarbonylative route for producing acetic acid or methyl acetate.

Yet another object of the present invention is to provide a process without corrosive iodide promoter for producing acetic acid or methyl acetate.

SUMMARY OF THE INVENTION

Accordingly the present invention provides a process for acetic acid or methyl acetate which comprises an iron and a tin containing compound with or without an organic compound containing C, N, O, P, S, diamine, diketone, and or diphosphines for producing acetic acid and or methyl acetate without an iodide promoter and without carbon monoxide in one pot reaction, with methanol as a reactant and nitrite or nitro compound as a solvent, at a reaction temperature.

In an embodiment of the present invention compound containing iron, a compound containing tin reacts with methanol in presence of nitrite or nitro compounds as solvent to produce acetic acid or methyl acetate.

In another embodiment of the present invention one or more coordinative nitrogen containing compound is used as a ligand along with the compound containing iron and a compound containing tin to produce acetic acid or methyl acetate.

In yet another embodiment of the present invention one or more coordinative phosphorous containing compound is used as a ligand along with the compound containing iron and a compound containing tin to produce acetic acid or methyl acetate.

In still another embodiment of the present invention one or more coordinative oxygen containing compound is used as a ligand.

In yet another embodiment of the present invention a coordinative sulfur containing compound is used as a ligand.

In still another embodiment of the present invention a coordinative carbon containing compound is used as a ligand.

DETAILED DESCRIPTION OF THE INVENTION

In the present invention an iron-containing compound is reacted with methanol in presence of a tin-containing compound and in presence or absence of a ligand. The reaction is effected in presence of a solvent. The principal object of the invention is to provide a process for the production of acetic acid and or methyl acetate from methanol with cheaper metal catalyst and without corrosive iodide promoter and without carbon monoxide.

The catalyst components as per the present invention contain a compound containing an iron, a compound containing tin and optionally a ligand.

An iron-containing compound in the present invention can be a metal complex of iron with an organic compound containing C, N, O, P, S, diamine, diketone, oxime, aldehyde, alcohol, phosphine and or diphosphine as a ligand.

The compound containing iron can also be a complex or a salt of iron, where iron is in oxidation state varying from 0 to 3.

The salt of iron can be a compound formed by the combination of iron and an anion.

The catalyst components as per the present invention contain a compound containing an iron, a compound containing tin and optionally a ligand. The tin-containing compound may be a salt of tin or a complex of tin, preferably a tin salt, like $SnX_2$ (wherein X represents a halogen atom).

An iron containing compound, a tin containing compound and a ligand containing one or more coordinative nitrogen atoms, coordinative phosphorous atoms, coordinative oxygen atoms, coordinative sulfar atoms, coordinative carbon atoms, or metal complex formed by a ligand containing one or more coordinative nitrogen atoms, coordinative phosphorous atoms, coordinative oxygen atoms, coordinative sulfur atoms, coordinative carbon atoms in the presence of methanol as a reacting material and a solvent are reacted together to produce acetic acid and or methyl acetate.

Examples of coordinative carbon containing ligand used in the present investigation include alkyl groups, aryl groups, arylalkyl groups, monovalent cyclic dienyl groups, such as a cyclopentadienyl group and a cyclooctadienyl group, olefins, CO group, and compounds represented by RCN (where R represents an alkyl group, a cycloalkyl group, an aryl group, an arylalkyl group or an alkoxyl group).

Examples of coordinative nitrogen atom used in the present invention include $NH_3$, amines (for example methylamine, ethyl amine, triphenyl amine, cyclohekyl amine, ethylenediamine, o-phenylenediamine), nitrogen containing heterocyclic compounds like pyridine, bipyridine, phenanthroline, imidazole, pyrimidine, piperazine piperidine, and morpholine).

Examples of oxime containing ligand are the condensation products of aldehyde and hydroxylamine.

A tetra dentate ligand containing oxygen and nitrogen as donor elements, are the examples of salen type of ligands. The salen structure is formed by condensation of salicylaldehyde and diamine compound having formula $H_2N(CH_2)nNH_2$ (wherein n represents a digit from 1 to 4) or aromatic diamines like o-phenylenediamine, as the examples of the present investigation.

Examples of coordinative phosphorous containing ligand used in the present invention include $PR_3$ or $OPR_3$ (wherein R represents an alkyl group, cycloalkyl group, an aryl group, an arylalkyl group, or an alkoxyl group) and bis(diphenylphosphino)alkanes such as 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane.

Examples of coordinative oxygen containing ligand include $H_2O$, alcohols including aliphatic alcohols and aromatic alcohols, aldehydes, ketones and diketones like acetyl acetonate.

Examples of coordinative sulfur containing ligand include ionic compounds containing thiocyanate group, MSCN (wherein M represents alkali metal), compounds represented by RSR and RSH (wherein R represents an alkyl group cycloalkyl group, an aryl group, arylalkyl group, and an alkoxyl group), and heterocyclic compounds containing sulfur atom.

Examples of the solvents used in the present investigation include the compounds containing nitrile group having general formula RCN (where R represents an alkyl group, a cycloalkyl group, an aryl group, an arylalkyl group or an alkoxyl group), the compounds containing nitro group having general formula $RNO_2$ (where R represents an alkyl group, a cycloalkyl group, an aryl group, an arylalkyl group or an alkoxyl group).

The catalyst components as per the present invention contain a compound containing an iron and a compound containing tin and optionally a ligand. The molar ratio of tin containing compound to the iron-containing compound in the reaction mixture can be for example from 1 to 30, preferably from 2 to 20. The ratio of methanol to the iron-containing compound is 10 to 800, preferably from 50 to 300. The ratio of methanol to the tin-containing compound is from 1 to 60, preferably from 2 to 20. The ratio of the ligand used to the iron-containing compound is from 0 to 10, preferably from 1 to 4 according to the coordinating sites of the ligand.

The catalyst formed by the combination of an iron compound a tin compound and a ligand can be reacted with methanol in presence of a solvent at a reaction temperature for example from 0 to 300° C., preferably from 40 to 200° C. The reaction can be effected in an inert atmosphere (for example, nitrogen helium, or argon) under atmospheric pressure or elevated pressure.

Thus, the catalyst formed insitu due to the addition of components described above can be used for the formation of acetic acid and or methyl acetate by reacting it with methanol in presence of a solvent as described above. The contact time of the reaction mixtures at the conditions described above can be from 1 hour to 72 hours, preferably from 1 to 24 hours.

The reaction in the present investigation proceeds as follows:

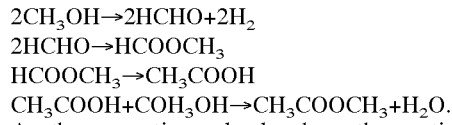

As these reactions clearly show the acetic acid thus formed further reacts with methanol employed as the starting material to give methyl acetate Therefore, suppressing the formation of methyl acetate by lowering the ratio of methanol in the reaction system can increase the formation of acetic acid.

In addition under some reaction conditions, methyl formate and methylal, which are useful compounds as precursors of acetic acid and methyl acetate, can also be formed. Accordingly the process of the present invention is usable also as a process for producing methyl formate and or methylal by appropriately selecting the reaction conditions. The formation of methylal is believed to proceed by the following way:

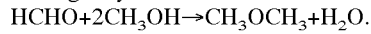

The following examples are given by way of illustration and therefore should not be construed to limit the scope of the present invention

EXAMPLE-1

In a 50 ml autoclave, $7.45 \times 10^{-4}$ mol ferrocene, 0.012 mol $SnCl_2.2H_2O$, 7.5 ml methanol, and 7.5 ml acetonitrile were charged. The autoclave was flushed with nitrogen and closed in the same environment. The contents were heated at 140° C. for 12 hours The autoclave was cooled to room temperature and then chilled in ice bath. The liquid phase of the reaction mixture was analyzed for methyl acetate as the product, by gas chromatography. The results of the gas chromatographic analysis showed 23.2% conversion of methanol with 15.7% yield of methyl acetate. The turnover number based on iron charged was found to be 14.5.

EXAMPLE-2

In a 50 ml autoclave, $7.45 \times 10^{-4}$ mol $FeCl_2.4H_2O$, 0.012 mol $SnCl_2.2H_2O$, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. The results of the gas chromatographic analysis indicated 23.2% conversion of methanol and 17% yield of methyl acetate. The turnover number was 14.5.

EXAMPLE-3

In a 50 ml autoclave, $7.45 \times 10^{-4}$ mol Fe(III) acetylacetonate, 0.012 mol $SnCl_2.2H_2O$, 7.5 ml methanol, and 7.5 ml acetonitrile were charged. The autoclave was flushed with nitrogen arid closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. The results indicated 34.3% conversion of methanol and 20.1% yield of methyl acetate. The turnover number was 16.1.

EXAMPLE-4

In a 50 ml autoclave, $7.45 \times 10^{-4}$ mol $FeCl_3$, 0.012 mol $SnCl_2.2H_2O$, 7.5 ml methanol and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. As a result 32.2% conversion of methanol, 23.5% yield of methyl acetate and 17 turnovers were observed.

EXAMPLE-5

In a 50 ml autoclave, $7.45 \times 10^{-4}$ mol $FeCl_3$, 0.012 mol $SnCl_2.2H_2O$, $7.45 \times 10^{-4}$ mol $PPh_3$, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. Gas chromatographic results indicated 20.7% conversion of methanol, 19.9% yield of methyl acetate and 14.2 turnovers.

EXAMPLE-6

In a 50 ml autoclave, $7.45 \times 10^{-4}$ mol $FeCl_3$, 0.012 mol $SnCl_2.2H_2O$, $7.45 \times 10^{-4}$ mol 1,2-bis(diphenylphosphino)ethane, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. As a result 21.3% conversion of methanol, 17.5% yield of methyl acetate and 14.5 turnovers were observed.

EXAMPLE-7

In a 50 ml autoclave, $7.45 \times 10^{-4}$ mol $FeCl_3$, 0.012 mol $SnCl_2.2H_2O$, $7.45 \times 10^{-4}$ mol $PPh_3$, 7.5 ml methanol, and 7.5 ml acetonitrile were charged. The autoclave was flushed with nitrogen and closed in the same environment, The contents were heated at 140° C. for 12 hours. The autoclave was cooled to room temperature and then chilled in ice bath. The liquid phase of the reaction mixture was analyzed for methyl acetate as the product, by gas chromatography. The results of the gas chromatographic analysis indicated 28.9% conversion of methanol and 24.1% yield of methyl acetate. The turnover number was 18.2

EXAMPLE-8

In a 50 ml autoclave, $7.45 \times 10^{-4}$ mol $FeCl_3$, 0.012 mol $SnCl_2.2H_2O$, $3.7225 \times 10^{-4}$ mol o-phenylenediamine, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. The results of the gas chromatographic analysis indicated 29.7% conversion of methanol and 23.8% yield of methyl acetate. The turnover number was 19.3.

EXAMPLE-9

In a 50 ml autoclave; $7.45 \times 10^{-4}$ mol $FeCl_3$, 0.012 mol $SnCl_2.2H_2O$, $3.7225 \times 10^{-4}$ mol salicylaldoxime, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath The liquid phase of the reaction mixture was analyzed for methyl acetate as the product, by gas chromatography. As a result 18.3% conversion of methanol, 19.4% yield of methyl acetate and 13.2 turnovers were observed.

EXAMPLE-10

In a 50 ml autoclave, $7.45 \times 10^{-4}$ mol $FeCl_3$, 0.012 mol $SnCl_2.2H_2O$, $7.45 \times 10^{-4}$ mol bis(salicylidene)ethylenediamine, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. As a result 17.0% conversion of methanol, 16.6% yield of methyl acetate and 13.7 turnovers were observed.

EXAMPLE-11

In a 50 ml autoclave, $7.45 \times 10^{-4}$ mol $FeCl_3$, 0.012 mol $SnCl_2.2H_2O$, $7.45 \times 10^{-4}$ mol potassium thiocyanate, 7.5 ml methanol, and 7.5 ml acetonitrile were charged; The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. As a result 31.4% conversion of methanol, 26.9% yield of methyl acetate and 19.5 turnovers were observed.

EXAMPLE-12

In a 50 ml autoclave, $7.45 \times 10^{-4}$ mol $FeCl_3$, 0.012 mol $SnCl_2.2H_2O$, $7.45 \times 10^{-4}$ mol thiophene, 7.5 ml methanol, and 7.5 ml acetonitrile were charged. The autoclave was flushed with nitrogen and closed in the same environment. The contents were heated at 140° C. for 12 hours. The autoclave was cooled to room temperature and then chilled in ice bath. The liquid phase of the reaction mixture was analyzed for methyl acetate as the product, by gas chromatography. As a result 34.4% conversion of methanol, 17% yield of methyl acetate and 10.4 turnovers were observed.

An iron containing compound with a tin containing compound is active for the production of acetic acid or methyl acetate. The process works in presence or in absence of various ligands.

The process is free from corrosive iodide promoters. The process does not need carbon monoxide.

The main advantages of the present invention are
1. The process in the invention reports a cheaper catalyst system for the production of acetic acid or methyl acetate.
2. The process is free from corrosive iodide promoters.
3. The process does not need carbon monoxide.
4. The process can be used for the production of methyl formate and methylal by selecting optimum operating conditions.

We claim:

1. A process for the preparation of acetic acid or methyl acetate comprising reacting methanol in the presence of a catalyst and a solvent at a reaction time and temperature, said solvent comprising a nitrile or nitro-containing compound and said catalyst comprising an iron-containing compound and a tin-containing compound, said reaction taking place in the absence of an iodide promoter, carbon monoxide and ruthenium, wherein said iron-containing compound is a complex or a salt of iron, wherein the iron is in an oxidation state of about 0 to 3 and said tin containing compound is complex or salt of tin.

2. The process of claim 1, wherein the molar ratio of the tin-containing compound to the iron-containing compound is about 1:1 to 30:1.

3. The process of claim 1, wherein the ligand is an organic compound containing one or more coordinative nitrogen atoms.

4. The process of claim 1, wherein the ligand is an organic compound containing one or more coordinative phosphorus atoms.

5. The process of claim 1, wherein the ligand is an organic compound containing one or more coordinative oxygen atoms.

6. The process of claim 1, wherein the ligand is an alkali metal salt containing a coordinative sulfur or an organic compound containing one or more coordinative sulfur atoms.

7. The process of claim 1, wherein the ligand is an organic compound containing one or more coordinative carbon atoms.

8. The process of claim 1, wherein the ligand is an organic compound containing one or more coordinative oxygen atoms and one or more coordinative nitrogen atoms.

9. The process of claim 1, wherein the temperature is in the range of about 0 to 300° C.

10. The process of claim 1, wherein the tin salt is represented by a formula $SnX_2$, wherein X is a halogen atom.

11. The process of claim 1, wherein said catalyst further contains a ligand.

12. The process of claim 3, wherein the coordinative nitrogen atom is $NH_3$, methylamine, ethylamine, triphenylamine, cyclohexylamine, ethylenediamine, o-phenylenediamine, pyridine, bipyridine, phenanthropline, pyrimidine, piperazine, piperidine or morpholine.

13. The process of claim 4, wherein the coordinative phosphorus atom is bis (diphenylphosphino)alkane or a compound represented by the formula $PR_3$ or $OPR_3$, wherein R represents an alkyl group, a cyclohexyl group, an aryl group, an arylalkyl group or an alkoxyl group.

14. The process of claim 5, wherein the coordinative oxygen atom is an $H_2O_2$ alcohol, an aldehyde, a ketone, or a diketone.

15. The process of claim 6, wherein the coordinative sulfur atom is an ionic compound containing a thiocyanate group, MSCN, wherein M represents an alkali metal, compounds represented by the formula RSR or RSH, wherein the R represents an alkyl group, a cycloalkyl group, an aryl group, and arylalkyl group and alkoxyl group, and heterocyclic compounds containing a sulfur atom.

16. The process of claim 7, wherein the coordinative carbon atom is an alkyl group, an aryl group, an arylalkyl group, a monovalent cyclic dienyl group, an olefin, a CO group and compounds represented by the formula RCN, wherein R represents an alkyl group, a cycloalkyl group, an aryl group or an alkoxyl group.

17. The process of claim 11, wherein the ligand is an oxime containing ligand.

18. The process of claim 11, wherein the ligand is a condensation product of salicylaldehyde and a diamine having the formula $H_2N(CH_2)_nNH_2$, wherein n represents an integer from 1 to 4 or the condensation product of salicylaldehyde and a aromatic diamine.

19. The process of claim 1, wherein the solvent is a compound having the formula RCN, wherein R represents an alkyl group, a cycloalkyl group, an aryl group, an arylalkyl group or an alkoxyl group or a compound having the formula $RNO_2$, wherein R represents an alkyl group, a cycloalkyl group, an aryl group, an arylalkyl group or an alkoxyl group.

20. The process of claim 2, wherein the molar ratio is about 2:1 to 20:1.

21. The process of claim 1, wherein the ratio of methanol to the iron-containing compound is about 10:1 to 800:1.

22. The process of claim 21, wherein the ratio is about 50:1 to 300:1.

23. The process of claim 1, wherein the ratio of methanol to the tin-containing compound is about 1:1 to 60:1.

24. The process of claim 23, wherein the ratio is 2:1 to 20:1.

25. The process of claim 11, wherein the ratio of ligand to iron-containing compound is about 0 to 10:1.

26. The process of claim 25, wherein the ratio is about 1:1 to 4:1.

27. The process of claims 9, wherein the reaction temperature is about 40 to 200° C.

28. The process of claim 1, wherein the reaction time is about 1 to 72 hours.

29. The process of claim 28, wherein the reaction time is about 1 to 24 hours.

30. The process of claim 1, wherein the reaction of methanol in the presence of a solvent and a catalyst is effected in an inert atmosphere.

* * * * *